United States Patent [19]

Kwan et al.

[11] Patent Number: 5,378,609

[45] Date of Patent: * Jan. 3, 1995

[54] LIPASE SINGLE REAGENT SYSTEM

[75] Inventors: Shing F. Kwan, Ventura; Rebecca J. Hunt, Carpinteria, both of Calif.

[73] Assignee: Ivan E. Modrovich, Camarillo, Calif.

[*] Notice: The portion of the term of this patent subsequent to Sep. 28, 2010 has been disclaimed.

[21] Appl. No.: 693,856

[22] Filed: Apr. 29, 1991

Related U.S. Application Data

[63] Continuation-in-part of Ser. No. 375,025, May 25, 1989, Pat. No. 5,248,598.

[51] Int. Cl.$^6$ ............................................. C12Q 1/34
[52] U.S. Cl. ................................ 435/18; 435/19; 252/312; 252/408.1
[58] Field of Search .................. 435/18, 19; 252/312, 252/408.1

[56] References Cited

U.S. PATENT DOCUMENTS

| | | | |
|---|---|---|---|
| 4,343,897 | 8/1982 | Neumann et al. | 435/19 |
| 4,847,376 | 7/1989 | Neumann et al. | 544/102 |
| 5,248,598 | 9/1993 | Kwan et al. | 435/18 |

OTHER PUBLICATIONS

Mizobuchi et al., *J. Neurochem.*, vol. 36(1), Jan. 1981, pp. 301–303.

*Primary Examiner*—Ronald W. Griffin
*Attorney, Agent, or Firm*—Christie, Parker & Hale

[57] ABSTRACT

A single system reagent for the determination of lipase, formulated as an emulsion comprising a lipase-active fatty acid source; a first lipase activator comprising colipase; a second lipase activator; a lipoprotein lipase inhibitor; an emulsion stabilizer comprising Triton X100; a buffer; and an antiprecipitant.

29 Claims, 2 Drawing Sheets

LIPASE SINGLE REAGENT SYSTEM

CROSS REFERENCE TO RELATED APPLICATIONS

This application is a continuation-in-part of U.S. application Ser. No. 07/357,025, filed May 25, 1989, now U.S. Pat. No. 5,248,598, issued Sep. 28, 1993.

FIELD OF THE INVENTION

This invention relates to a single system reagent for the determination of lipase by turbidimetric method.

BACKGROUND OF THE INVENTION

Human pancreatic lipase is a glycoprotein with a molecular mass of approximately 45,000 daltons. Lipase cleaves emulsified long-chain triglycerides to yield mono-and diglycerides, and fatty acids. It is known that cleavage of triglycerides by lipase only occurs at the oil/water interface of an oil in water emulsion. In other words, lipase activity is manifested only on the boundary surface of oil droplets existing as the dispersed phase in a continuous water phase. Lipase-induced cleavage of triglycerides is affected by substrate surface phenomena.

As an indication of both acute and chronic pancreatitis, pancreatic cancer, pancreatic injury, and miscellaneous abdominal disorders, a patient's serum and tissue lipase activity is a powerful diagnostic tool. Because of lipase's unique reaction mechanism, however, the diagnostic usefulness of lipase depends on the method used for its estimation. used for its estimation.

Several methods for serum lipase assay are known. Older methods, such as the Cherry-Crandall method, required overnight sample incubation and time-consuming titration to a color-change end point. Because of the numerous steps involved, the procedures tended to suffer from poor reproducibility.

Variations on the Cherry-Crandall method have been reported; their primary limitation is the triglyceride emulsion. Because lipase activity varies with the overall surface area of the oil droplets in the emulsion, reproducible results were difficult to obtain. Even with the best efforts, the emulsions employed in these methods varied from batch to batch.

Another problem with early assay methods is their indifference to lipoprotein lipase interference. Particularly among patients receiving the drug heparin, falsely increased lipase values have resulted when lipoprotein lipase interference has not been accounted for.

Turbidimetric methods for lipase determination are known. In a typical turbidimetric assay, a sample of lipase-containing serum is mixed with a predetermined amount of a triglyceride-water emulsion, and the clarification of the turbidity of the emulsion is followed photometrically.

Although turbidimetric techniques have proven to be both more reliable and more convenient than older titrimetric serum lipase tests, the techniques suffer from certain drawbacks. The primary problem is due to non-uniformity of the size of the emulsified oil droplets. To permit spectrophotometry, the emulsion must be very dilute. Negative lipase values occasionally result, because increases in optical absorbance are obtained during the measurement phase of the test.

Attempts to improve the turbidimetric technique by solving the problem of droplet size non-uniformity are known. U.S. Pat. No. 4,343,897 to Neumann et al., incorporated herein by reference, describes a dry reagent for the turbidimetric determination of lipase, which forms an emulsion when water is added thereto. The dry reagent is prepared by lyophilization of an emulsion produced by conventional methods. The composition of U.S. Pat. No. 4,343,897 relies on disappearance of the substrate as a measure of lipase concentration. U.S. Pat. No. 4,847,376, also to Neumann, et al. and incorporated herein by reference, discloses colormetric substrates for use in such emulsion systems. Both suffer from the expense of lyophilization and from the inherent drawback of potential human error in the reconstitution of the emulsions.

Accordingly, a need exists for a reagent for the determination of lipase that gives consistently uniform results, is easily prepared in toto in the factory, and is ready to use in the field as a single system reagent. The present invention fulfills this need.

SUMMARY OF THE INVENTION

A single system reagent for the determination of lipase is provided. The reagent is formulated as an emulsion comprising a substrate, preferably a lipase-active fatty acid source such as a triglyceride, a first lipase activator comprising colipase, a second lipase activator, a lipoprotein lipase inhibitor, an emulsion stabilizer comprising Triton X100, and if desired, another emulsion stabilizer, a buffer, and an anti-precipitant. The emulsion can be prepared in toto in the factory and is ready to use in the field as a complete reagent for the turbidimetric determination of lipase.

More specifically, sodium chloride and/or calcium chloride serve as additional activators. A bile acid salt, such as sodium deoxycholate, acts as a lipoprotein lipase inhibitor. Triton X100, a required emulsion stabilizer, is a polyethylene glycol p-isooctylphenyl ether. A second emulsion stabilizer, if employed, is preferably urea. A zwiterionic buffer is preferred with 2-amino-2-hydroxymethyl-1,3-propanediol, commonly known as TRIS or TRIS-buffer, being the presently preferred buffer. Brij-35, a polyoxyethylene ether, is the preferred anti-precipitant. A microbial growth retardant, such as sodium azide, may also be added to the formulation.

The reagent is prepared by first compounding an aqueous component comprising colipase, calcium chloride and/or sodium chloride, a bile acid salt, a buffer, a microbial growth retardant, and an anti-precipitant. An oil-based component comprising a lipase-active fatty acid source and Triton X100 (as a stabilizer) is compounded separately. The two components are separately filtered and then combined, with agitation, to form a uniform, ready-to-use emulsion.

The lipase single reagent systems of the instant invention are stable for at least about twelve days at 56° C. which corresponds to a lifetime of at least two years at 4° C., which is more than ample to account for the time shipment of the product to any part of the world and storage up to the time of use. Moreover an assay can be completed within ten minutes, as required for commercial acceptability.

DETAILED DESCRIPTION

Figure 1:
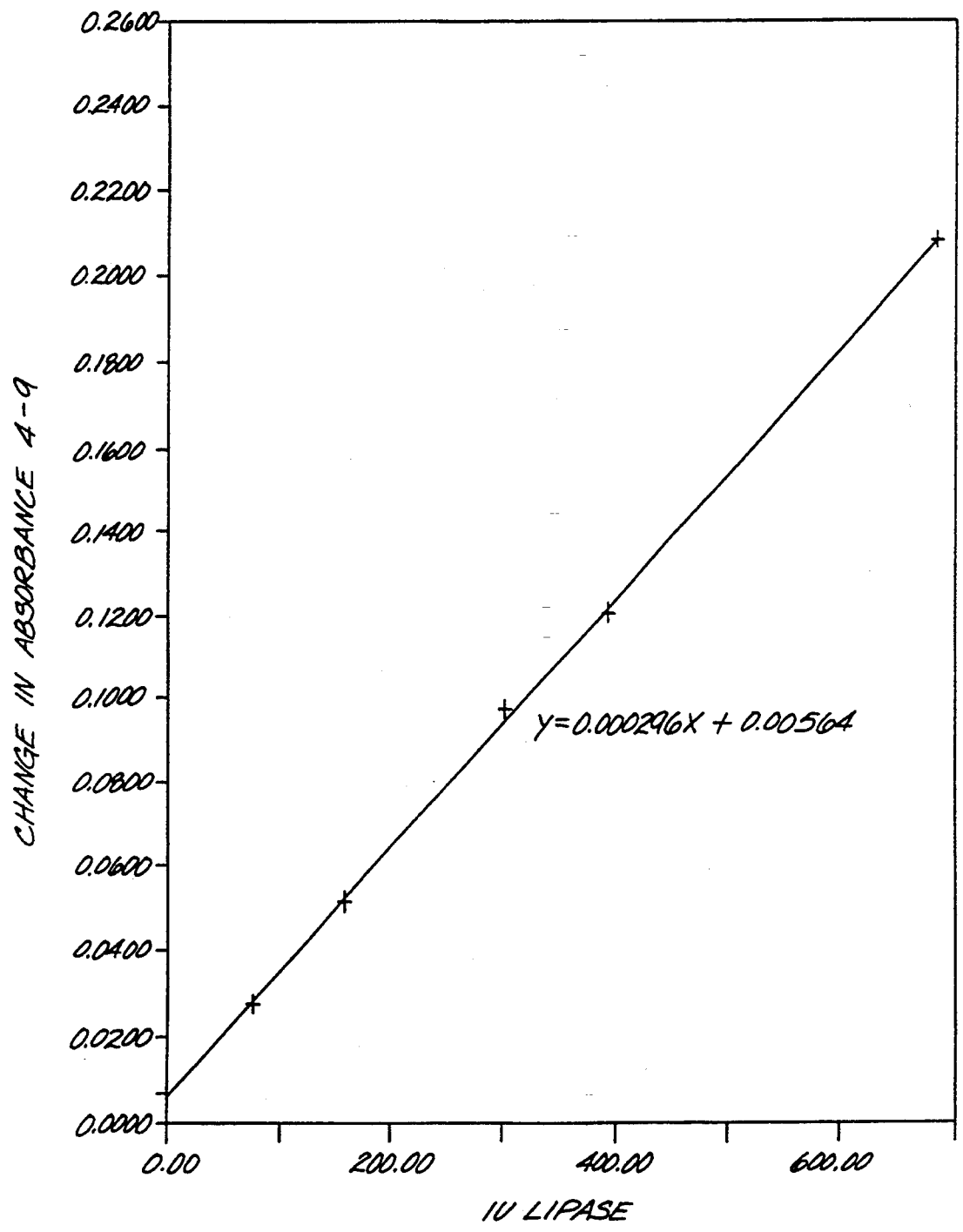
FIG. 1 shows the linear relationship between sample lipase concentration and change in optical absorbance obtainable with compositions of the invention.

There is provided a single system reagent for the turbidimetric determination of lipase. The reagent is formulated as a convenient, ready-to-use emulsion that can be prepared in toto and quality control of which exists in a factory. The emulsion comprises a substrate, preferably a lipase-active fatty acid source; a colipase as lipase activator, used alone or with another lipase activator such as alkali or alkali earth chloride; a lipoprotein lipase inhibitor; an emulsion stabilizer comprising Triton X100, used alone or with another emulsion stabilizer such as urea; a buffer; and an anti-precipitant. A microbial growth retardant may also be and is preferably present.

Useful substrates include lipase-active fatty acid sources such as long chain triglycerides, short or medium chain mono- or triglycerides, and tweens (polyoxyethylene ethers of mixed partial oleic esters of sorbitol anhydrides). Long chain triglycerides (triglycerides having fatty acid residues with C-14 to about C-25 chain lengths) are preferred, because they are preferentially cleaved by lipase. In contrast, the other mentioned substrates are also subject to cleavage by carboxylesterases. Triolein, a triglyceride having C-17 fatty acid fragments, is the presently preferred triglyceride. Olive oil is yet another useful lipase-active fatty acid source. Acceptable reagent formulations can be prepared with lipase-active fatty acid source concentrations ranging from about 0.2 to about 0.4 mM. Preferably, the fatty acid source comprises an alcohol solution thereof. n-Pentanol is a preferred solvent.

Other useful substrates are described in U.S. Pat. No. 4,847,376 to Neumann, et al., incorporated herein by reference, which are cleaved by lipase to yield hydroxy or a thiol compound which is optically detectable directly or when coupled to chromophore to enable lipase concentration in sera to be determined.

Cleavage of triglycerides and other substrates by lipase is known to occur only at the oil and water interface of an emulsion in which the oil is the discontinuous phase and water is the continuous phase. Compounds which prevent the approach of lipase to the emulsified triglycerides have an inhibitory effect on lipase activity. Bile salts, phospholipids, and free fatty acids, having both polar and nonpolar regions, tend to concentrate at the interface and inhibit lipase. Proteins, such as albumin, have a similar effect, probably owing to lipids bound to albumin which are attracted to the hydrophobic phase.

In the present invention, colipase, a 10,000 Dalton molecule, is used as a lipase activator and overcomes the inhibitory effect of lipase blocking agents by "anchoring" lipase to lipid globules. Preferred colipase concentrations range from about 70 to about 590 U/ml.

In addition to colipase, the reagent comprises a second lipase activator selected from the group consisting of alkali chlorides, alkaline earth chlorides, and mixtures thereof. Preferably calcium chloride is used. Although sodium chloride is a lipase inhibitor in concentrations of 100 mM and higher, in the presence of colipase and bile salts its inhibitory effect is eliminated. In concentrations of from about 20 to 40 mM, sodium chloride is a lipase activator. Similarly, lipase activity is increased when the reagent contains calcium. Calcium helps maintain linear reaction kinetics and additionally facilitates emulsion stability. Presently preferred calcium concentrations range from about 0.05 to about 0.5 mM.

As noted above, the presence of lipoprotein lipase in some test samples interferes with the accurate determination of lipase. In order to inhibit the effect of lipoprotein lipase, it is desirable to include a bile acid or a salt thereof in the reagent. The bile acid ordinarily inhibits both lipase and lipoprotein lipase activity; however, in the presence of colipase, the effect on lipase activity is nullified. Suitable bile acid salts include deoxycholates and taurodeoxycholates. Sodium deoxycholate is preferred. The preferred bile acid or bile acid salt concentrations range from about 15 to about 30 mM.

An emulsion stabilizer is also present. It is preferred to utilize a polyethylene glycol p-isooctylphenyl ether, sold commercially as Triton X100. This class of compounds has the general formula: $CH_3C(CH_3)_2CH_2C(CH_3)_2-C_6H_6-O(CH_2CH_2O)_xH$, with an average composition of $C_{34}H_{62}O_{11}$. Triton X100 is employed in a concentration of from about 0.025 to about 0.13 percent by weight of the total composition. While not discounting that other equivalents exist, it has been found that Triton X100 is unique in its ability to insure long-term stability of the emulsion of the instant invention.

A second emulsion stabilizer may be employed and, when used, is preferably urea in a concentration of from about 0.01 to about 1.0 percent by weight of the emulsion.

In order to control the pH of the reagent, a buffer is added. The presently preferred buffers are zwiterionic agents, most preferably 2-amino-2-hydroxy-methyl-1,3-propanediol, known as TRIS. Acceptable buffer concentrations range from about 0.025 to about 0.13 percent by weight of the emulsion.

To further stabilize the reagent, and to prevent precipitation of human sera samples, an antiprecipitant, such as a polyoxyethelene ether of an aliphatic alcohol (sold commercially as the "Brij" line of surfactants) is added. A preferred antiprecipitant is Brij-35: polyoxyethylene (23) lauryl ether. Preferred antiprecipitant concentrations range from about 0.02 to about 0.2 percent by weight.

In addition to the above constituents, it is desirable to include a microbial growth retardant within the reagent. A preferred retardant is sodium azide, in a concentration of from about 0.05 to about 0.2 percent by weight. Alternatively, sulfur-containing preservatives can be used.

The invention has been described above as a compilation of components, and conditions, each of which has a broad acceptable range of concentrations or values. Optimization studies were carried out in order to determine preferred and optimal values of each component within the prepared emulsion. The results are given in Table 1.

The present invention also comprises a method for the preparation of a single system reagent for the determination of lipase. The method comprises the following steps:

An oil-based component is prepared by mixing a lipase active fatty acid source with a first emulsion stabilizer comprising Triton X100.

The oil-based component is filtered.

An aqueous component is prepared by combining a first lipase activator comprising colipase; a second lipase activator (e.g. sodium chloride, calcium chloride and mixtures thereof); a lipoprotein lipase inhibitor; a second emulsion stabilizer comprising, e.g. urea; a buffer (e.g. 2-amino-2-hydroxymethyl-1,3-propanediol); and an antiprecipitant (e.g. Brij-35). Preferably, the aqueous component also comprises a microbial-growth retardant, such as sodium azide.

The aqueous component is filtered.

A stable emulsion is formed by mixing a filtered oil-based component with a filtered aqueous component. The aqueous component to oil-based component ratio is from about 40:1 to about 200:1. The result is a convenient-to-use, single reagent system that may be used in the turbidimetric determination of lipase.

In one embodiment of the invention, the pH of the aqueous component is adjusted prior to the formation of the emulsion. Acceptable results are achieved when the pH is within the range of about 8.8 to about 9.6. Preferably, the pH is within the range of about 9.0 to about 9.4; optimal results are realized at pH range of 9.2 to 9.4.

TABLE 1

| Component or Parameter | Range | One Preferred | Presently Preferred |
|---|---|---|---|
| Substrate; Triolein | 0.25–0.35 mM | 0.305 mM | 0.309 mM |
| Colilpase[1] | 70–890 U/ml | 171.3 U/ml | 298.5 U/ml |
| Sodium Chloride | 0–35 mM | 32.300 mM | 0 |
| Calcium Chloride | 0.15–0.25 mM | 0.195 mM | 0.199 mM |
| Sodium Deoxycholate[2] | 17–25 mM | 19.500 mM | 19.900 mM |
| Triton X100[3] | 0.05–0.1% | 0.074% | 0.062% |
| Urea | 0.9–0.5% | 0.500% | 0 |
| Tris[4] | 17–22 mM | 19.500 mM | 19.900 mM |
| Brij-35[5] | 0.04–0.1% | 0.058% | 0.06% |
| Sodium Azide | 0.08–0.12% | 0.098% | 0.1% |
| pH | 9.0–9.5 | 9.2 | 9.35–9.4 |

[1]Commercially available from Kodak Chemical Co. one unit of colipase is defined as the amount of enzyme needed to release 1 mole of fatty acid per minute from tributyrin at 25° C.
[2]Sodium salt of deoxycholic acid.
[3]A polyethylene glycol p-isooctylphenyl ether, manufactured and sold by Rohm and Haas Co.
[4]2-amino-2-hydroxymethyl-1,3-propanediol, manufactured and sold by Commercial Solvents Corp.
[5]Polyoxyethylene (23) lauryl ether, manufactured and sold by ICI United States, Inc.

The following Examples are given for the purpose of illustrating the present invention.

EXAMPLE 1

An aqueous solution is prepared by dissolving the following components in distilled water to the indicated concentrations: 171 U/ml colipase, 0.2 mM calcium chloride, 20 mM sodium deoxycholate, 0.25 percent by weight urea, 20 mM Tris buffer, 35 mM sodium chloride, 0.1 percent by weight sodium azide, and 0.06 percent by weight Brij-35. The pH of the solution is adjusted to 9.2 and the solution is filtered. An oil-based component is prepared by forming an n-propanol solution containing 12.5 mM triolein and three percent by weight Triton X100. This component is filtered. A working emulsion is formed by mixing the aqueous component with the oil-based component in a 40:1 ratio. The composition of the working emulsion is shown in Table 2.

TABLE 2

| Component | Concentration |
|---|---|
| Colipase | 171 U/ml |
| Calcium Chloride | 0.195 mM |
| Sodium Deoxycholate | 19.50 mM |
| Triolein | 0.305 mM |
| Urea | 0.244% |

TABLE 2-continued

| Component | Concentration |
|---|---|
| Triton X100 | 0.074% |
| Tris | 19.50 mM |
| Sodium Chloride | 32.20 mM |
| Sodium Azide | 0.098% |
| Brij-35 | 0.058% |

The working emulsion was assayed for linearity. The results are shown in FIG. 1. As indicated, the reagent prepared as in Example 1 is linear to at least 700 I.U. of lipase. In other words, accurate lipase determinations are obtained over a broad range of lipase concentrations. Good turbidimetric sensitivity and linearity is obtained when approximately 40 ul of sample is mixed with one ml of reagent; a sensitivity of about $1.1 \times 10^{-4}$ ABS units/I.U. lipase/minute is achieved for this sample to reagent ratio.

The temporal stability of the reagent has been determined. An emulsion was compounded in the manner described in Example 1 and stressed at varying temperatures. The reagent to sample ratio was 2 ml:0.080 ml. Samples were human sera of controlled lipase content. Turbidimetric measurements were performed at 340 nm at 37° C., with a reaction time of four minutes. The results are shown in Table 3.

TABLE 3

| Temperature | Absorbance | | |
|---|---|---|---|
| | Day 3 | Day 12 | Day 14 |
| Ai | | | |
| 4° C. | 1.5167 | NA | NA |
| Room Temp. | NA | NA | 1.4150 |
| 41° C. | NA | NA | 1.2603 |
| 47° C. | 1.4720 | NA | 1.4056 |
| 57° C. | 1.5136 | 1.4590 | NA |
| Blank | | | |
| 4° C. | 0.0011 | NA | NA |
| Room Temp. | NA | NA | 0.0017 |
| 41° C. | NA | NA | 0.0012 |
| 47° C. | 0.0014 | NA | 0.0014 |
| 57° C. | 0.0017 | 0.0016 | NA |

NA = Not Assayed.

As indicated in Table 3, the emulsion is stable for a minimum of 14 days at 47° C. and 12 days at 57° C. which corresponds to a lifetime in excess of two years at 4° C.

EXAMPLE 2 AND CONTROL

Triton X100 as a stabilizer and an antiprecipitant are essential components of time-stable lipase assay compositions of our invention and are required to achieve a product having essentially linear performance (response) with age. To establish the importance of the ability to form a liquid time-stable lipase single reagent system, two formulations were prepared. The first duplicated Example 2 of U.S. Pat. No. 4,343,897. The reagents were compounded in the same ratios given, but because of an inability to lyophilize the substrate, the substrate was added quickly with rapid stirring to the second solution which contained urea. The combined mixture was stirred until homogenous emulsion formed. For evaluation purposes, it was designated as the "Control." To illustrate the time stability of the compositions of the invention of the above-identified application, a composition was formed which contained as the stabilizing surfactant Triton X100, and as the precipitation retardant Brij-35. There was formed an emulsion of the composition and properties shown in Table 4.

TABLE 4

| | |
|---|---|
| 19.900 mM | Sodium Deoxycholate |
| 0.199 mM | Calcium Chloride |
| 19.900 mM | |
| 0.0995% | Sodium Azide |
| 0.0597% | Brij-35 |
| 298.5 U/ml | Colipase |
| 0.062% | Triton X100 |
| 0.309 mM | Triolein |
| pH 9.35 to 9.40 | |

Figure 2:
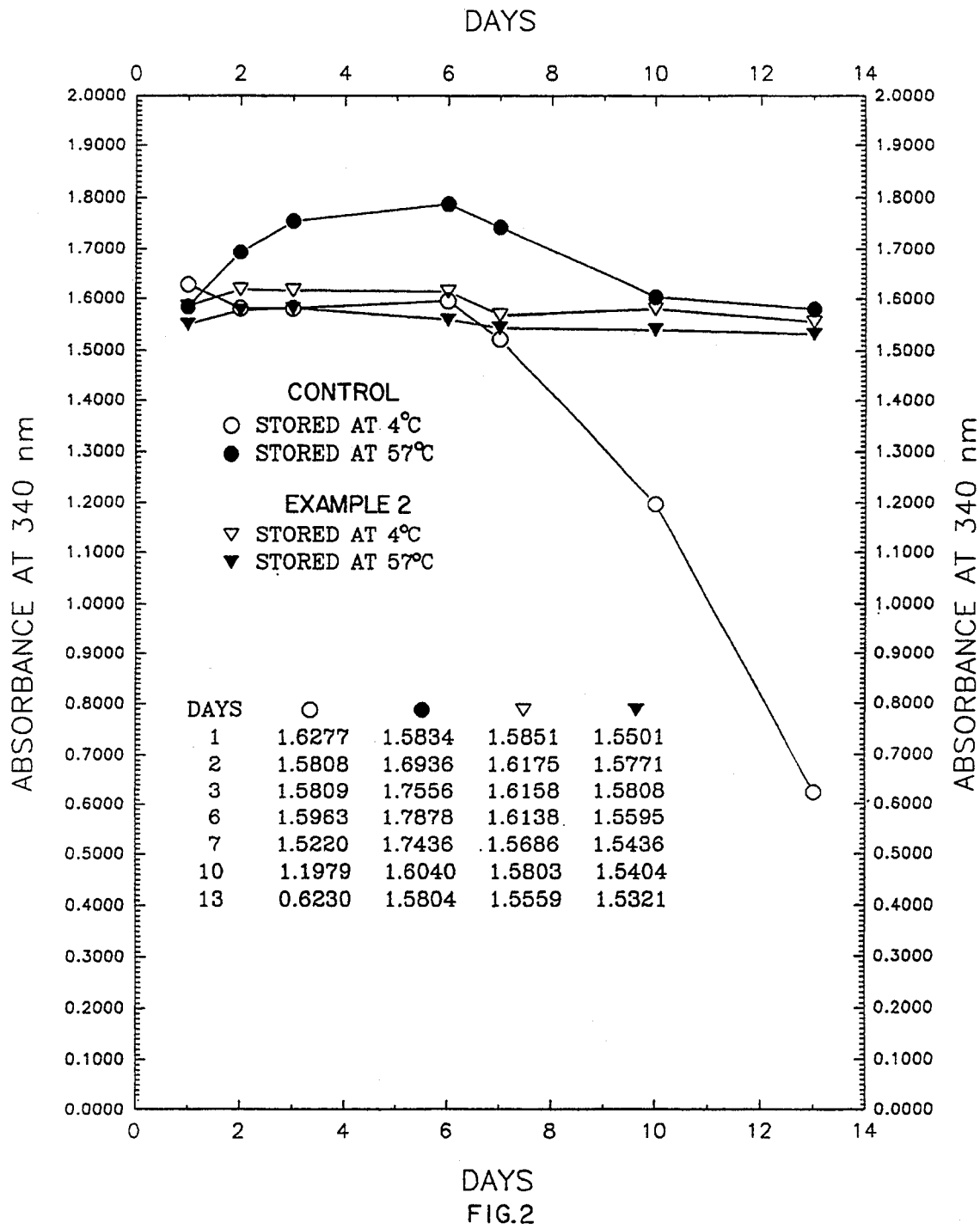
FIG. 2 shows the time stability of the presently preferred composition of this invention in comparison to the composition of Example 2 of U.S. Pat. No. 4,343,897 to Neumann, et al.

This is known, for purposes of the evaluation, as Example 2. Samples of the Example 2 and Control compositions were each stored at 4° C. and at 57° C., and absorbance readings were taken after storage from 1, 2, 3, 6, 7, 10 and 13 days. The results are shown in the attached FIG. 2.

The absorbance readings for Example 2 showed an essentially linear response with time (age). This meant that the composition remained essentially unchanged in activity throughout an aging or stress time frame representing normal use, namely storage at 4° C., and after a storage equivalent of four years at 4° C., namely in excess of 12 days at 56°–57° C. The linear absorbance shown in FIG. 2 means that the composition will be expected to give the same reading when used to assay a lipase content of human sera in the as-prepared state and after storage under normal refrigeration conditions for a period of years. The emulsion showed no signs of degradation.

With respect to the Control, the emulsion began to degrade within seven days storage at 4° C. When exposed to stress at 57° C., a sample of the Control increased in absorbance almost immediately. This was caused by a precipitation of one or more ingredients in the composition, probably polyethylene glycol 4000. The increase in absorbance is as important a detriment as a decrease in absorbance, as both introduce commercially unacceptable errors to an assay for quantitative determination of lipase in human sera. The precipitate that formed did not go back into the solution, and the emulsion continued to break apart. Not only did the emulsion decay, it also lost functional capabilities. On day 6, a control lipase calibrator having a lipase content equivalent of 422 U/l was assayed with each of the test samples. Table 5 shows the change of absorbance in (ABS) units per minute. The difference in change for Example 2 stressed at 4° C. and 57° C. was a commercially acceptable 4%. The difference in change in absorption for the Control was a commercially unacceptable 25%.

TABLE 5

| Sample | Stress Temp | Absorbance, nm | Percent Change |
|---|---|---|---|
| Example 2 | 4° C. | 0.0295 | |
| Example 2 | 57° C. | 0.221 | 25% |
| Control | 4° C. | 0.211 | |
| Control | 57° C. | 0.203 | 4% |

The invention has been described in exemplary and preferred embodiments, but is not limited thereto. Those skilled in the art will recognize that a number of additional modifications and improvements can be made without departure from the essential spirit and scope of the invention. Therefore, the invention is not limited by the above disclosure, but only by the following claims.

What is claimed is:

1. A single emulsion reagent for the determination of lipase comprising:
   a lipase substrate;
   a lipase activator comprising colipase as a first lipase activator comprising colipase provided in an amount sufficient to anchor lipase to liquid globules;
   an activating amount of a second lipase activator selected from the group consisting of alkaline earth chlorides, and mixtures of alkaline earth chlorides and alkali chlorides;
   a lipoprotein lipase inhibitor selected from the group consisting of bile acid and bile acid salts;
   a stabilizing amount of an emulsion stabilizer comprising Triton X-100, a polyethylene glycol p-isooctyl-phenyl ether;
   a buffer present in an amount sufficient to maintain a pH in the range of from about 8.8 to about 9.6; and
   an antiprecipitant present in an amount sufficient to prevent precipitation of constituents of human sera.

2. A reagent as claimed in claim 1, wherein the substrate is a triglyceride.

3. A reagent as claimed in claim 2, wherein the triglyceride has fatty acid residues containing from 14 to 25 carbon atoms.

4. A reagent as claimed in claim 2, wherein the triglyceride is triolein.

5. A reagent as claimed in claim 1, wherein the substrate source has a concentration of from about 0.2 to about 0.4 mM.

6. A reagent as claimed in claim 1, wherein the colipase is present in a concentration of from about 70 to about 590 U/ml.

7. A reagent as claimed in claim 1, wherein the alkaline earth chloride is calcium chloride.

8. A reagent as claimed in claim 1, wherein the second lipase activator comprises from about 0.05 to about 0.35 mM calcium chloride.

9. A reagent as claimed in claim 1, wherein the lipoprotein lipase inhibitor comprises a bile acid salt.

10. A reagent as claimed in claim 9, wherein the bile acid salt is a deoxycholate present in a concentration of from about 15 to about 30 mM.

11. A reagent as claimed in claim 10, wherein the bile acid salt is sodium deoxycholate.

12. A reagent as claimed in claim 1, wherein the Triton X100 is present in a concentration of from about 0.025 to about 0.13 percent by weight of the emulsion.

13. A reagent as claimed in claim 1, wherein an additional emulsion stabilizer is present.

14. A reagent as claimed in claim 1, wherein the buffer comprises 2-amino-2-hydroxymethyl-1,3-propanediol in a concentration of from about 15 to about 30 mM.

15. A reagent as claimed in claim 1, wherein the antiprecipitant comprises a polyoxyethylene ether of a higher aliphatic alcohol.

16. A reagent as claimed in claim 15, wherein the polyoxyethylene ether is polyoxyethylene (23) lauryl ether.

17. A reagent as claimed in claim 15, wherein the polyoxyethylene ether has a concentration of from about 0.02 to about 0.2 percent by weight.

18. A reagent as claimed in claim 1, further comprising a microbial growth retardant.

19. A reagent as claimed in claim 18, wherein the microbial growth retarder comprises sodium azide.

20. A reagent as claimed in claim 18, wherein the microbial growth retarder has a concentration of from about 0.05 to about 0.2 percent by weight.

21. A single system reagent for the determination of lipase, formulated as an emulsion comprising:
   from about 0.25 to about 0.35 mM triolein;
   from about 100 to about 350 U/ml colipase;
   from about 0.15 to about 0.25 mM calcium chloride;
   from 0 to about 35 mM sodium chloride;
   from about 17 to about 25 mM deoxycholate;
   from about 0.05 to about 0.1 percent by weight Triton X 100, a polyethylene glycol p-isooctyl-phenyl ether;
   from 0 to about 0.5 percent by weight urea;
   from about 17 to 22 mM 2-amino-2-hydroxymethyl-1,3-propanediol; and from about 0.04 to about 0.1 percent by weight polyoxyethylene (23) lauryl ether.

22. A reagent as claimed in claim 21, further comprising from about 0.08 to about 0.12 percent by weight sodium azide.

23. A time-stable single reagent system for the determination of lipase, formulated as an emulsion comprising:
   about 0.309 mM triolein;
   about 298.5 U/ml colipase;
   about 0.199 mM calcium chloride;
   about 19.9 mM deoxycholate;
   about 0.062 percent by weight Triton X100, a polyethylene glycol p-isooctyl-phenyl ether;
   about 19.9 mM 2-amino-2-hydroxymethyl-1,3-propanediol;
   about 0.06 percent by weight polyoxyethylene (23) lauryl ether; and
   about 0.1 percent by weight sodium azide.

24. A reagent as claimed in claim 1 formed of an aqueous phase and an oil phase in which the ratio of the aqueous phase to the oil phase is from 40:1 to 200:1.

25. A reagent as claimed in claim 23 formed of an aqueous phase and an oil phase in a ratio of from 40:1 to 200:1.

26. A single system reagent for the determination of lipase, prepared by:
   forming an oil-based component by mixing a lipase active fatty acid source with a first emulsion stabilizer comprising Triton X100, a polyethylene glycol p-isooctylphenyl ether;
   filtering the oil-based component;
   forming an aqueous component by combining a first lipase activator comprising colipase; a second lipase activator selected from the group consisting of sodium chloride, calcium chloride, and mixtures thereof; a lipoprotein lipase inhibitor; a buffer; a microbial growth retardant, and an antiprecipitant;
   filtering the aqueous component; and
   forming a stable emulsion by mixing the filtered oil-based component with the filtered aqueous component.

27. A single system reagent as claimed in claim 26, wherein the aqueous component is adjusted to a pH of from about 8.8 to about 9.6 prior to filtering.

28. A reagent as claimed in claim 27, wherein the pH is within the range of from about 9.0 to about 9.5.

29. A reagent as claimed in claim 27, wherein the pH is adjusted to about 9.2 to about 9.4.

* * * * *

UNITED STATES PATENT AND TRADEMARK OFFICE
CERTIFICATE OF CORRECTION

PATENT NO. : 5,378,609
DATED : January 3, 1995
INVENTOR(S) : Shing F. Kwan; Rebecca J. Hunt It is certified that error appears in the above-indentified patent and that said Letters Patent is hereby corrected as shown below:

On the Title page, Item 63, after "5,248,598" insert
-- , which is a continuation-in-part
of Ser. No. 292,654, Dec. 28, 1988,
Pat. No. 5,011,867 --.

Column 1, line 8, after "Sep. 28, 1993" insert
-- , which is a continuation-in-part of
U.S. application Ser. No. 07/292,654, filed
December 28, 1988, now U.S. Pat. No. 5,011,867,
issued Apr. 30, 1991 --.

Column 1, line 32, after "estimation." (first occurrence)
delete "used for its estimation."
Column 2, Line 9, change "colormetric" to
-- colorimetric --.
Column 2, line 63, change "DRAWING" to -- DRAWINGS --.
Column 6, line 16, change "40 ul" to -- 40 $\mu$l --.
Column 6, line 57, after "first" insert -- formulation --.
Column 9, line 13, change "X 100" to -- X100 --.

Signed and Sealed this

Thirteenth Day of August, 1996

Attest:

BRUCE LEHMAN

Attesting Officer

Commissioner of Patents and Trademarks